(12) United States Patent
Haury et al.

(10) Patent No.: US 11,738,152 B2
(45) Date of Patent: Aug. 29, 2023

(54) MULTI-USE DISPOSABLE SYSTEM AND SYRINGE THEREFOR

(71) Applicant: BAYER HEALTHCARE LLC, Whippany, NJ (US)

(72) Inventors: John Haury, Sewickley, PA (US); Alison R. Von Moger, Ashfield (AU); Mark Silvio Profaca, West Pymble (AU)

(73) Assignee: BAYER HEALTHCARE, LLC, Whippany, NJ (US)

( * ) Notice: Subject to any disclaimer, the term of this patent is extended or adjusted under 35 U.S.C. 154(b) by 269 days.

(21) Appl. No.: 16/304,850

(22) PCT Filed: Jun. 12, 2017

(86) PCT No.: PCT/US2017/036941
§ 371 (c)(1),
(2) Date: Nov. 27, 2018

(87) PCT Pub. No.: WO2017/218372
PCT Pub. Date: Dec. 21, 2017

(65) Prior Publication Data
US 2020/0268980 A1     Aug. 27, 2020

Related U.S. Application Data

(60) Provisional application No. 62/350,487, filed on Jun. 15, 2016.

(51) Int. Cl.
*A61M 5/315* (2006.01)
*A61M 5/31* (2006.01)
*A61M 5/145* (2006.01)

(52) U.S. Cl.
CPC .... *A61M 5/31566* (2013.01); *A61M 5/14566* (2013.01); *A61M 5/3134* (2013.01); *A61M 5/3137* (2013.01); *A61M 2005/3139* (2013.01)

(58) Field of Classification Search
CPC .............. A61M 5/007; A61M 5/14546; A61M 5/16827; A61M 5/14566; A61M 5/1456; A61M 2005/14553
See application file for complete search history.

(56) References Cited

U.S. PATENT DOCUMENTS

| | | |
|---|---|---|
| 926,755 A | 7/1909 | Nathaniel |
| 2,287,746 A | 6/1942 | Morton |

(Continued)

FOREIGN PATENT DOCUMENTS

| | | |
|---|---|---|
| CA | 1126117 A | 6/1982 |
| DE | 3838689 C1 | 6/1990 |

(Continued)

OTHER PUBLICATIONS

Asepti-Quik S Connector Catalog, May 2010.

(Continued)

*Primary Examiner* — Emily L Schmidt
(74) *Attorney, Agent, or Firm* — David Schramm; Joseph L. Kent; James R. Stevenson

(57) ABSTRACT

A syringe including a syringe body extending from a proximal end to a distal end, and a stabilizing element provided on the distal end of the syringe body, a portion of the stabilizing element extending substantially perpendicular to a longitudinal axis of the syringe body. A multi-use disposable set (MUDS) includes a plurality of syringes, each syringe having a syringe body, a proximal end, a distal end spaced apart from the proximal end along a longitudinal axis of the syringe body, a stabilizing element provided on the distal end, a portion of the stabilizing element extending substantially perpendicular to the longitudinal axis of the syringe body, and a manifold in fluid communication with the distal end of each of the plurality of syringes.

2 Claims, 14 Drawing Sheets

(56) References Cited

U.S. PATENT DOCUMENTS

| | | |
|---|---|---|
| 2,731,053 A | 1/1956 | Lockhart |
| 2,780,243 A | 2/1957 | Williams et al. |
| 2,798,487 A | 7/1957 | Ferguson |
| 2,938,238 A | 5/1960 | Gewecke et al. |
| 2,997,043 A | 8/1961 | Flynn |
| 3,164,279 A | 1/1965 | Towns |
| 3,658,061 A | 4/1972 | Hall |
| 3,835,862 A | 9/1974 | Villari |
| 3,909,910 A | 10/1975 | Rowe et al. |
| 3,985,133 A | 10/1976 | Jenkins et al. |
| 3,986,508 A | 10/1976 | Barrington |
| 3,987,930 A | 10/1976 | Fuson |
| 4,019,512 A | 4/1977 | Tenczar |
| 4,022,205 A | 5/1977 | Tenczar |
| 4,106,654 A | 8/1978 | Jones |
| 4,123,091 A | 10/1978 | Cosentino et al. |
| 4,187,846 A | 2/1980 | Carminucci et al. |
| 4,194,509 A | 3/1980 | Ferguson et al. |
| 4,227,615 A | 10/1980 | Flick |
| 4,230,231 A | 10/1980 | Burnett et al. |
| 4,340,148 A | 7/1982 | Beckham |
| 4,360,969 A | 11/1982 | Collier |
| 4,366,816 A | 1/1983 | Bayard et al. |
| 4,369,779 A | 1/1983 | Spencer |
| 4,396,385 A | 8/1983 | Kelly et al. |
| 4,398,757 A | 8/1983 | Floyd et al. |
| 4,402,420 A | 9/1983 | Chernack |
| 4,433,973 A | 2/1984 | Kurtz et al. |
| 4,450,624 A | 5/1984 | Collier |
| 4,482,347 A | 11/1984 | Borsanyi |
| 4,511,359 A | 4/1985 | Vaillancourt |
| 4,551,146 A | 11/1985 | Rogers |
| 4,559,043 A | 12/1985 | Whitehouse et al. |
| 4,579,823 A | 4/1986 | Ryder |
| 4,624,664 A | 11/1986 | Peluso et al. |
| 4,636,204 A | 1/1987 | Christopherson et al. |
| 4,687,472 A | 8/1987 | Gross |
| 4,723,945 A | 2/1988 | Theiling |
| 4,775,369 A | 10/1988 | Schwartz |
| 4,778,447 A | 10/1988 | Velde et al. |
| 4,795,426 A | 1/1989 | Jones |
| 4,810,241 A | 3/1989 | Rogers |
| 4,828,557 A | 5/1989 | Persidsky |
| 4,854,836 A | 8/1989 | Borsanyi |
| 4,883,641 A | 11/1989 | Wicks et al. |
| 4,950,260 A | 8/1990 | Bonaldo |
| 4,981,469 A | 1/1991 | Whitehouse et al. |
| 5,049,047 A | 9/1991 | Polaschegg et al. |
| 5,057,088 A | 10/1991 | Narayanan et al. |
| 5,088,984 A | 2/1992 | Fields |
| 5,098,395 A | 3/1992 | Fields |
| 5,102,253 A | 4/1992 | Pugliesi-Conti et al. |
| 5,171,229 A | 12/1992 | McNeil et al. |
| 5,184,742 A | 2/1993 | Decaprio et al. |
| 5,213,483 A | 5/1993 | Flaherty et al. |
| 5,221,267 A | 6/1993 | Folden |
| 5,251,873 A | 10/1993 | Atkinson et al. |
| 5,280,809 A | 1/1994 | Tive |
| 5,281,111 A | 1/1994 | Plambeck et al. |
| 5,292,308 A | 3/1994 | Ryan |
| 5,340,359 A | 8/1994 | Segura Badia |
| 5,382,242 A | 1/1995 | Horton et al. |
| 5,413,280 A | 5/1995 | Taylor |
| 5,482,171 A | 1/1996 | Palmer |
| 5,494,036 A | 2/1996 | Uber, III et al. |
| 5,498,253 A | 3/1996 | Aswad et al. |
| 5,551,850 A | 9/1996 | Williamson et al. |
| 5,569,181 A | 10/1996 | Heilman et al. |
| 5,620,433 A | 4/1997 | Aswad et al. |
| 5,739,508 A | 4/1998 | Uber, III |
| 5,746,718 A | 5/1998 | Steyn |
| 5,779,675 A | 7/1998 | Reilly et al. |
| 5,785,691 A | 7/1998 | Vetter et al. |
| 5,803,510 A | 9/1998 | Dorsey, III et al. |
| 5,806,519 A | 9/1998 | Evans, III et al. |
| 5,840,026 A | 11/1998 | Uber, III et al. |
| 5,843,037 A | 12/1998 | Uber, III |
| 5,853,096 A | 12/1998 | Bartur et al. |
| 5,873,861 A | 2/1999 | Hitchins et al. |
| 5,913,434 A | 6/1999 | Fukuhara et al. |
| 5,916,197 A | 6/1999 | Reilly et al. |
| 5,934,496 A | 8/1999 | Mogard et al. |
| 5,964,583 A | 10/1999 | Danby |
| 5,972,292 A | 10/1999 | Demeo |
| 6,077,259 A | 6/2000 | Caizza et al. |
| 6,113,068 A | 9/2000 | Ryan |
| 6,123,686 A | 9/2000 | Olsen et al. |
| 6,164,279 A | 12/2000 | Tweedle |
| 6,261,270 B1 | 7/2001 | Gault et al. |
| 6,306,117 B1 | 10/2001 | Uber, III |
| 6,339,718 B1 | 1/2002 | Zatezalo et al. |
| 6,428,518 B1 | 8/2002 | Brengle et al. |
| 6,436,072 B1 | 8/2002 | Kullas et al. |
| 6,511,472 B1 | 1/2003 | Hayman et al. |
| 6,616,000 B1 * | 9/2003 | Renz ................. A61J 9/001 |
| | | 215/11.1 |
| 6,666,839 B2 | 12/2003 | Utterberg et al. |
| 6,669,681 B2 | 12/2003 | Jepson et al. |
| 6,679,529 B2 | 1/2004 | Johnson et al. |
| 6,814,726 B1 | 11/2004 | Lauer |
| 6,821,267 B2 | 11/2004 | Veillon et al. |
| 6,869,425 B2 | 3/2005 | Briggs et al. |
| 6,911,025 B2 | 6/2005 | Miyahara |
| 6,981,960 B2 | 1/2006 | Cho et al. |
| 7,022,256 B2 | 4/2006 | Uegami et al. |
| 7,040,598 B2 | 5/2006 | Raybuck |
| 7,070,589 B2 | 7/2006 | Ebner et al. |
| 7,083,605 B2 | 8/2006 | Miyahara |
| 7,097,209 B2 | 8/2006 | Unger et al. |
| 7,241,285 B2 | 7/2007 | Dikeman |
| 7,252,308 B2 | 8/2007 | Thilly |
| 7,361,156 B2 * | 4/2008 | Joyce ............... A61M 5/14546 |
| | | 604/131 |
| 7,374,555 B2 | 5/2008 | Heinz et al. |
| 7,452,349 B2 | 11/2008 | Miyahara et al. |
| 7,481,795 B2 | 1/2009 | Thompson et al. |
| 7,569,047 B2 | 8/2009 | Utterberg |
| 7,618,412 B2 | 11/2009 | Chernack |
| 7,713,250 B2 | 5/2010 | Harding et al. |
| 7,731,155 B2 | 6/2010 | Funamura et al. |
| 7,740,288 B2 | 6/2010 | Mantell |
| 7,918,243 B2 | 4/2011 | Diodati et al. |
| 7,938,454 B2 | 5/2011 | Buchanan et al. |
| 8,007,487 B2 | 8/2011 | Patrick et al. |
| 8,012,144 B2 | 9/2011 | Moberg |
| 8,038,667 B2 | 10/2011 | Racz et al. |
| 8,062,009 B2 | 11/2011 | Cueni |
| 8,133,035 B2 | 3/2012 | Wolff |
| 8,140,274 B2 | 3/2012 | Gagel et al. |
| 8,147,464 B2 | 4/2012 | Spohn et al. |
| 8,157,547 B2 | 4/2012 | Oude et al. |
| 8,257,267 B2 | 9/2012 | Thornton |
| 8,287,724 B2 | 10/2012 | Slepicka et al. |
| 8,308,456 B2 | 11/2012 | Moubayed |
| 8,343,128 B2 | 1/2013 | Nagao et al. |
| 8,360,757 B2 | 1/2013 | Knauper et al. |
| 8,425,463 B2 | 4/2013 | Patrick et al. |
| 8,545,440 B2 | 10/2013 | Patrick et al. |
| 8,852,162 B2 | 10/2014 | Williams et al. |
| 9,044,542 B2 | 6/2015 | Patrick et al. |
| 9,358,333 B2 | 6/2016 | Trombley, III et al. |
| 9,393,441 B2 | 7/2016 | Hoffman et al. |
| 9,408,971 B2 | 8/2016 | Carlyon et al. |
| 9,566,381 B2 | 2/2017 | Barron et al. |
| 10,046,106 B2 | 8/2018 | Cowan et al. |
| 2001/0016704 A1 | 8/2001 | Zadno-Azizi et al. |
| 2002/0010437 A1 | 1/2002 | Lopez et al. |
| 2002/0093192 A1 | 7/2002 | Matkovich |
| 2004/0122369 A1 | 6/2004 | Schriver et al. |
| 2005/0090805 A1 | 4/2005 | Shaw et al. |
| 2005/0199304 A1 | 9/2005 | Poppe et al. |
| 2005/0267418 A1 | 12/2005 | Fournie et al. |
| 2007/0049870 A1 | 3/2007 | Gray et al. |

(56) References Cited

U.S. PATENT DOCUMENTS

| | | |
|---|---|---|
| 2007/0088271 A1* | 4/2007 | Richards .......... A61M 5/14244 604/151 |
| 2007/0100282 A1* | 5/2007 | Small ................ G16H 20/17 604/151 |
| 2008/0045925 A1 | 2/2008 | Stepovich et al. |
| 2008/0071219 A1 | 3/2008 | Rhinehart et al. |
| 2008/0071220 A1 | 3/2008 | Rhinehart et al. |
| 2008/0097342 A1 | 4/2008 | Gordin |
| 2008/0177250 A1 | 7/2008 | Howlett et al. |
| 2008/0287872 A1 | 11/2008 | Patzer |
| 2009/0102192 A1 | 4/2009 | Ziman |
| 2009/0105629 A1 | 4/2009 | Grant et al. |
| 2009/0182309 A1 | 7/2009 | Muffly |
| 2009/0216192 A1 | 8/2009 | Schriver et al. |
| 2010/0022988 A1 | 1/2010 | Wochner et al. |
| 2010/0049170 A1 | 2/2010 | Solomon et al. |
| 2010/0056975 A1 | 3/2010 | Dale et al. |
| 2010/0113924 A1 | 5/2010 | Hajicek et al. |
| 2010/0116365 A1 | 5/2010 | McCarty |
| 2010/0130918 A1 | 5/2010 | Elahi |
| 2010/0130922 A1 | 5/2010 | Borlaug et al. |
| 2010/0286467 A1 | 11/2010 | Pesach et al. |
| 2010/0305508 A1 | 12/2010 | Franks et al. |
| 2011/0049866 A1 | 3/2011 | Trombley, III et al. |
| 2011/0054440 A1 | 3/2011 | Lewis |
| 2011/0196291 A1 | 8/2011 | Vischer et al. |
| 2011/0240158 A1 | 10/2011 | Py |
| 2011/0282302 A1 | 11/2011 | Lopez et al. |
| 2011/0313394 A1 | 12/2011 | Bobo, Sr. |
| 2012/0116317 A1 | 5/2012 | Kassab et al. |
| 2012/0123257 A1* | 5/2012 | Stokes, Jr. .......... A61M 5/1782 600/432 |
| 2012/0148415 A1 | 6/2012 | Brueckner et al. |
| 2013/0079581 A1 | 3/2013 | Agamaite et al. |
| 2013/0123567 A1 | 5/2013 | Agamaite et al. |
| 2013/0131579 A1 | 5/2013 | Mantell et al. |
| 2013/0211248 A1* | 8/2013 | Cowan ................ A61M 5/1452 600/432 |
| 2013/0245565 A1* | 9/2013 | Leak .................... A61M 5/19 604/246 |
| 2013/0331634 A1 | 12/2013 | Kaintz et al. |
| 2014/0107480 A1 | 4/2014 | Spohn et al. |
| 2014/0224829 A1 | 8/2014 | Capone et al. |
| 2014/0296786 A1* | 10/2014 | Servansky .......... A61M 5/1456 604/152 |
| 2014/0342447 A1 | 11/2014 | Aviles et al. |
| 2015/0174338 A1 | 6/2015 | Takemoto |
| 2017/0056603 A1 | 3/2017 | Cowan et al. |
| 2017/0266373 A1* | 9/2017 | Pananen .......... A61M 5/14566 |

FOREIGN PATENT DOCUMENTS

| | | |
|---|---|---|
| DE | 4037797 C1 | 2/1992 |
| DE | 102013104018 A1 | 10/2014 |
| EP | 0204977 A1 | 12/1986 |
| EP | 0503670 A2 | 9/1992 |
| EP | 1331020 A1 | 7/2003 |
| EP | 2409720 A1 | 1/2012 |
| EP | 1834664 B1 | 5/2013 |
| FR | 2594496 A1 | 8/1987 |
| FR | 2847342 A1 | 5/2004 |
| GB | 2020735 A | 11/1979 |
| JP | 2003210574 A | 7/2003 |
| WO | 9103404 A1 | 3/1991 |
| WO | 9714493 A1 | 4/1997 |
| WO | 9806446 A2 | 2/1998 |
| WO | 0202164 A1 | 1/2002 |
| WO | 0204049 A1 | 1/2002 |
| WO | 02096487 A1 | 12/2002 |
| WO | 03039646 A1 | 5/2003 |
| WO | 03044488 A1 | 5/2003 |
| WO | 2005110007 A2 | 11/2005 |
| WO | 2008086631 A1 | 7/2008 |
| WO | 2008141337 A1 | 11/2008 |
| WO | 2009067200 A2 | 5/2009 |
| WO | 2009149367 A1 | 12/2009 |
| WO | 2012170961 A1 | 12/2012 |
| WO | 2013043868 A1 | 3/2013 |
| WO | 2013043881 A1 | 3/2013 |
| WO | 2013059563 A1 | 4/2013 |
| WO | 2013104665 A1 | 7/2013 |
| WO | WO-2015058088 A1 * | 4/2015 ........... A61M 5/007 |
| WO | WO2015-066506 * | 5/2015 ........... A61M 5/178 |

OTHER PUBLICATIONS

AseptiQuik X Connector Catalog, Oct. 2012.
Catalog Valves, http://www.minivalve.com/newsite/index.php/en/home—last visited Sep. 23, 2016.
COLDER; Products Company., "Asepti-Quik Product Catalog", accessed online on Oct. 11, 2013.
Connection Solutions for Biopharmaceutical Processes, May 2012.
DoseGuard Valved Bottle Adapter System Brochure.
"Extended European Search Report and Written Opinion from EP14810311", dated Nov. 22, 2016.
"Extended European Search Report from EP App. No. 16735394", dated Dec. 11, 2018.
Hadaway; Lynn, "Needleless Connectors: A Primer on Terminology", Journal of Infusion Nursing, Jan./Feb. 2010, 33(1), 22-31.
"International Preliminary Report on Patentability and Written Opinion from PCT Application No. PCT/US2012/060978", dated Apr. 22, 2014.
"International Preliminary Report on Patentability from PCT Application No. PCT/US2015/010825", dated Jul. 21, 2016.
"International Preliminary Report on Patentability from PCT Application No. PCT/US2017/036941", dated Dec. 27, 2018.
International Preliminary Report on Patentability, Written Opinion, and International Search Report from PCT/US2014/042310 dated Dec. 15, 2015.
"International Search Report and Written Opinion from corresponding PCT App. No. PCT/US2015/010825", dated Apr. 10, 2015.
"International Search Report and Written Opinion from PCT Application No. PCT/US2014/044500", dated Nov. 4, 2014.
"International Search Report and Written Opinion from PCT Application No. PCT/US2017/036941", dated Sep. 12, 2017.
"International Search Report from PCT Application No. PCT/US2012/060978", dated Feb. 5, 2013.
"International Search Report in PCT Application No. PCT/US2014/044500", dated Nov. 4, 2014.
Pure Fit SC True Sterile Connections . . . Outside the Clean Room Catalog, Saint-Gobain Performance Plastics. 2008.
ReadyMate Disposable Aseptic Connectors, Operation Manual, Jul. 2009.
Single-Use Bags 50 to 500 Liters Catalog, Jun. 2010.
Site-Scrub IPA Device—last visited Sep. 23, 2016.
TAKEONE Aseptic Sampling System Brochure, 2010.
UFP; Technologies., "BioShell Suspension Pack Brochure", accessed online on May 7, 2013.
"ULTRAPORT Swabbable Port Stopcocks, B. Braun Sharing Expertise.", accessed online on Apr. 14, 2014.
"Supplementary European Search Report from EP Application No. 15735396", dated Jun. 28, 2017.
"Supplementary European Search Report from EP Application No. EP12842335.", dated Feb. 16, 2015.
"Written Opinion and International Search Report from PCT Application No. PCT/US2016/012434", dated May 6, 2016.

* cited by examiner

MULTI-USE DISPOSABLE SYSTEM AND SYRINGE THEREFOR

CROSS REFERENCE TO RELATED APPLICATION

This application is a 371 national phase application of PCT International Application No. PCT/US2017/036941, filed Jun. 12, 2017, and claims the benefit of U.S. Provisional Patent Application No. 62/350,487 titled MULTI-USE DISPOSABLE SYSTEM AND SRYINGE THEREFOR, filed Jun. 15, 2016, the disclosures of which are incorporated herein by reference in their entirety.

BACKGROUND

Field of the Technology

This disclosure relates, generally, to the field of multi-fluid delivery systems and, more particularly, to syringes used in a multi-use disposable set of a multi-fluid delivery system.

Description of Related Art

In many medical diagnostic and therapeutic procedures, a medical practitioner, such as a physician, injects a patient with one or more medical fluids. In recent years, a number of medical fluid delivery systems for pressurized injection of fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other imaging procedures. In general, these medical fluid delivery systems are designed to deliver a preset amount of fluid at a preset flow rate.

In some injection procedures, the medical practitioner places a catheter or needle into a vein or artery of the patient. The catheter or needle is connected to either a manual or an automatic fluid injector system by way of tubing, and a connector that interfaces with the fluid injector system. Automatic fluid injector systems typically include at least one syringe connected to at least one fluid injector having, for example, a powered linear piston. The at least one syringe includes, for example, a source of contrast and/or a source of flushing fluid. The medical practitioner enters settings into an electronic control system of the fluid injector for a fixed volume of contrast and/or saline and a fixed rate of injection for each. A single-use disposable set connector and associated tubing is connected to the fluid injector system for delivering one or more fluids to the patient.

While various manual and automatic fluid delivery systems are known in the medical field, improved multi-fluid delivery systems adapted for use in medical diagnostic and therapeutic procedures where one or more fluids are supplied to a patient during such procedures continue to be in demand. Additionally, improved syringes that may be used with multi-fluid delivery systems for facilitating a delivery of one or more fluids to a patient are also desired in the medical field. The medical field continues to demand improved medical devices and systems used to supply fluids to patients during various medical procedures.

SUMMARY

In view of the foregoing, a need exists for an improved multi-use disposable set and syringe therefor that allows for more stable positioning of the syringe within a fluid injector. Further, there is a need for an improved syringe that prevents a situation where force applied to the syringe(s) of the multi-use disposable set during fluid deliver or force applied when engaging the multi-use disposable set into the injector may push or dislodge the multi-use disposable set into an off-center, tilted, or angled position within the fluid delivery system. In such an off-center, tilted, or angled position, additional for may cause fluid leakage around the plunger, breakage of the multi-use disposable set, or damage to portions of the fluid injector assembly.

Therefore, a multi-use disposable set and syringe therefor configured to address some or all of these needs are provided herein. According to a first example of the disclosure, a syringe may include a syringe body having a proximal end and a distal end spaced apart from the proximal end along a longitudinal axis, a cone portion and a nozzle extending distally from the distal end of the syringe body, and a stabilizing element provided on the distal end of the syringe body, the stabilizing element having a support surface extending substantially perpendicular to the longitudinal axis of the syringe body.

The stabilizing element may be integrally formed on the syringe body. The stabilizing element may include a ring provided on an outer circumferential surface of the distal end of the syringe body. The stabilizing element may include a sleeve provided on an outer circumferential surface of the syringe body. The sleeve may extend from the proximal end of the syringe body to the distal end of the syringe body. The stabilizing element may include a portion of the syringe body that extends axially along a longitudinal axis of the syringe body and protrudes from the cone portion on a distal end of the syringe body. The stabilizing element may include a planar portion and at least two webs connected to the cone portion and the planar portion. The stabilizing element may include at least two substantially triangular extensions including an upper planar surface and a bottom surface connected to the cone portion. The upper planar surface may extend substantially perpendicularly relative to the longitudinal axis of the syringe body. The stabilizing element may include a first planar portion connected to the cone portion via at least one web, and a second planar portion connected to the cone portion via at least one web. The planar portions may be separated from one another on the cone portion. The planar portions may extend substantially perpendicularly relative to the longitudinal axis of the syringe body. The planar portions may be positioned adjacent a discharge conduit defined in the distal end of the syringe body.

In another example of the disclosure, a multi-use disposable set (MUDS) may include a plurality of syringes, each syringe having a syringe body, proximal end, a distal end spaced apart from the proximal end along a longitudinal axis of the syringe body, a cone portion and a nozzle extending distally from the distal end of the syringe body, a stabilizing element provided on the distal end, the stabilizing element having a support surface extending substantially perpendicular to the longitudinal axis of the syringe body, and a manifold in fluid communication with the distal end of each of the plurality of syringes.

The stabilizing element may be integrally formed on the syringe body. The stabilizing element may include a ring provided on an outer circumferential surface of the distal end of the syringe body. The stabilizing element may include a sleeve provided on an outer circumferential surface of the syringe body. The sleeve may extend from the proximal end of the syringe body to the distal end of the syringe body. The stabilizing element may include a portion of the syringe body that extends axially along a longitudinal axis of the syringe body and protrudes from the cone portion on a distal end of the syringe body. The stabilizing element may include a planar portion and at least two webs connected to the cone portion and the planar portion. The stabilizing element may include at least two substantially triangular extensions including an upper planar surface and a bottom surface connected to the cone portion. The upper planar surface may extend substantially perpendicularly relative to the longitudinal axis of the syringe body. The stabilizing element may include a first planar portion connected to the cone portion via at least one web, and a second planar portion connected to the cone portion via at least one web. The planar portions may be separated from one another on the cone portion. The planar portions may extend substantially perpendicularly relative to the longitudinal axis of the syringe body. The planar portions may be positioned adjacent a discharge conduit defined in the distal end of the syringe body.

Further examples will now be described in the following numbered clauses.

Clause 1: A syringe, comprising a syringe body having a proximal end and a distal end spaced apart from the proximal end along a longitudinal axis; a cone portion and a nozzle extending distally from the distal end of the syringe body; and a stabilizing element provided on the distal end of the syringe body, the stabilizing element having a support surface extending substantially perpendicular to the longitudinal axis of the syringe body.

Clause 2: The syringe of Clause 1, wherein the stabilizing element is integrally formed on the syringe body.

Clause 3: The syringe of Clause 1 or Clause 2, wherein the stabilizing element comprises a ring provided on an outer circumferential surface of the distal end of the syringe body.

Clause 4: The syringe of any of Clauses 1-3, wherein the stabilizing element comprises a sleeve provided on an outer circumferential surface of the syringe body, the sleeve extending from the proximal end of the syringe body to the distal end of the syringe body.

Clause 5: The syringe of any of Clauses 1-4, wherein the stabilizing element comprises a portion of the syringe body that extends axially along a longitudinal axis of the syringe body and protrudes from the cone portion on a distal end of the syringe body.

Clause 6: The syringe of any of Clauses 1-5, wherein the stabilizing element comprises a planar portion and at least two webs connected to the cone portion and the planar portion.

Clause 7: The syringe of any of Clauses 1-6, wherein the stabilizing element comprises at least two substantially triangular extensions including an upper planar surface and a bottom surface connected to the cone portion.

Clause 8: The syringe of Clause 7, wherein the upper planar surface extends substantially perpendicularly relative to the longitudinal axis of the syringe body.

Clause 9: The syringe of any of Clauses 1-8, wherein the stabilizing element comprises a first planar portion connected to the cone portion via at least one web, and a second planar portion connected to the cone portion via at least one web, and wherein the planar portions are separated from one another on the cone portion.

Clause 10: The syringe of Clause 9, wherein the planar portions extend substantially perpendicularly relative to the longitudinal axis of the syringe body, and wherein the planar portions are positioned adjacent to a discharge conduit defined in the distal end of the syringe body.

Clause 11: A multi-use disposable set (MUDS) comprising: a plurality of syringes, each syringe having a syringe body, a proximal end, a distal end spaced apart from the proximal end along a longitudinal axis of the syringe body, a cone portion and a nozzle extending distally from the distal end of the syringe body, and a stabilizing element provided on the distal end, the stabilizing element having a support surface extending substantially perpendicular to the longitudinal axis of the syringe body; and a manifold in fluid communication with the distal end of each of the plurality of syringes.

Clause 12: The MUDS of Clause 11, wherein the stabilizing element is integrally formed on the syringe body.

Clause 13: The MUDS of Clause 11 or Clause 12, wherein the stabilizing element comprises a ring provided on an outer circumferential surface of the distal end of the syringe body.

Clause 14: The MUDS of any of Clauses 11-13, wherein the stabilizing element comprises a sleeve provided on an outer circumferential surface of the syringe body, the sleeve extending from the proximal end of the syringe body to the distal end of the syringe body.

Clause 15: The MUDS of any of Clauses 11-14, wherein the stabilizing element comprises a portion of the syringe body that extends axially along a longitudinal axis of the syringe body and protrudes from the cone portion on a distal end of the syringe body.

Clause 16: The MUDS of any of Clauses 11-15, wherein the stabilizing element comprises a planar portion and at least two webs connected to the cone portion and the planar portion.

Clause 17: The MUDS of any of Clauses 11-16, wherein the stabilizing element comprises at least two substantially triangular extensions including an upper planar surface and a bottom surface connected to the cone portion.

Clause 18: The MUDS of Clause 17, wherein the upper planar surface extends substantially perpendicularly relative to the longitudinal axis of the syringe body.

Clause 19: The MUDS of any of Clauses 11-18, wherein the stabilizing element comprises a first planar portion connected to the cone portion via at least one web, and a second planar portion connected to the cone portion via at least one web, and wherein the planar portions are separated from one another on the cone portion.

Clause 20: The MUDS of Clause 19, wherein the planar portions extend substantially perpendicularly relative to the longitudinal axis of the syringe body, and wherein the planar portions are positioned adjacent to a discharge conduit defined in the distal end of the syringe body.

These and other features and characteristics of multi-use disposable sets and syringes therefor, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure. As used in the specification and the claims, the singular form of "a", "an", and "the" include plural referents unless the context clearly dictates otherwise.

DETAILED DESCRIPTION

Figure 1A:
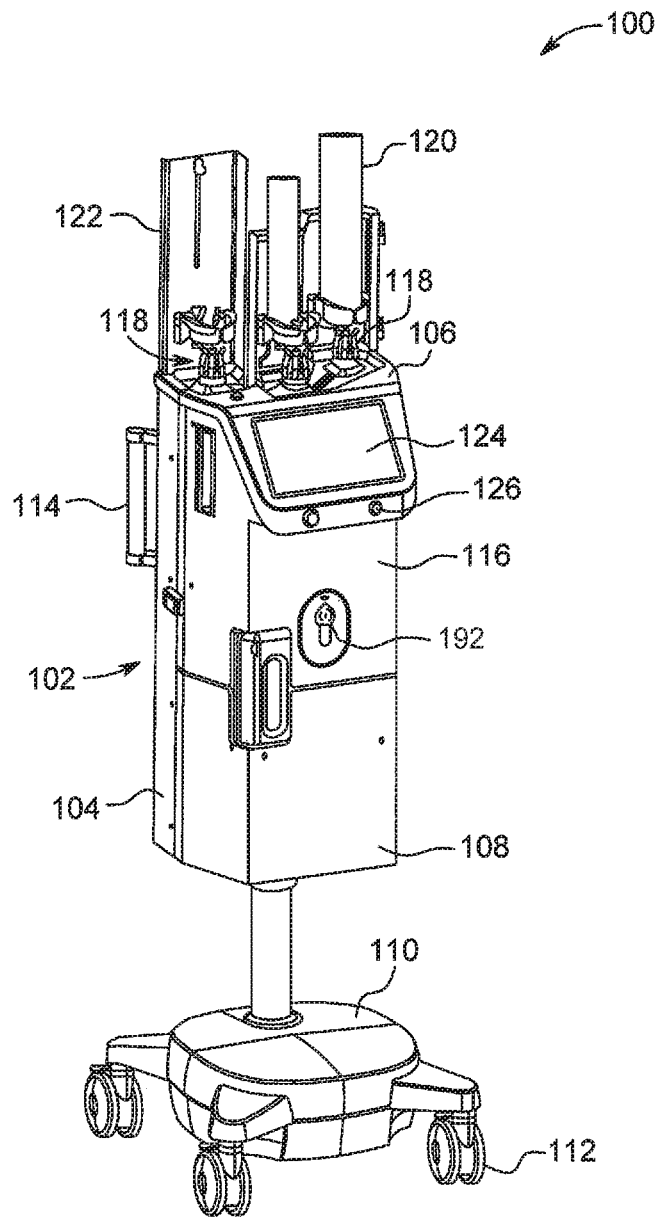
FIG. 1A is a perspective view of a multi-fluid delivery system, according to one example of the disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe of a fluid injector of a MUDS, the term "proximal" refers to a portion of a syringe nearest a piston element when the MUDS is installed on a fluid injector system. When used in relation to a syringe of a MUDS, the term "distal" refers to a portion of a syringe nearest to a delivery nozzle or any portion of a syringe from a delivery nozzle to at least a midway point on a body of the syringe. It is also to be understood that the specific devices and processes illustrated in the attached drawings, and described in the following specification, are simply exemplary examples of the disclosure. Hence, specific dimensions and other physical characteristics related to the examples disclosed herein are not to be considered as limiting.

Referring to the drawings in which like reference characters refer to like parts throughout the several views thereof, the present disclosure is generally directed to a multi-fluid medical injector/injection system 100 (hereinafter "fluid injector system 100") having a multi-use disposable set (MUDS) 130 configured for delivering fluid to a patient using a single-use disposable set (SUDS) connector. The fluid injector system 100 includes multiple components as individually described herein. Generally, the fluid injector system 100 has a powered injector administrator or device and a fluid delivery set intended to be associated with the injector to deliver one or more fluids from one or more multi-dose containers under pressure into a patient, as described herein. The various devices, components, and features of the fluid injector system 100, and the fluid delivery set associated therewith are likewise described in detail herein.

With reference to FIG. 1A, the fluid injector system 100 includes an injector housing 102 having opposed lateral sides 104, a distal or upper end 106, and a proximal or lower end 108. In some examples, the housing 102 may be supported on a base 110 having one or more wheels 112 for rotatable and movable support of the housing 102 on a floor surface. The one or more wheels 112 may be lockable to prevent the housing 102 from inadvertently moving once positioned at a desired location. At least one handle 114 may be provided to facilitate moving and positioning the fluid injector system 100. In other examples, the housing 102 may be removably or non-removably secured to a fixed surface, such as a floor, ceiling, wall, or other structure. The housing 102 encloses the various mechanical drive components, electrical and power components necessary to drive the mechanical drive components, and control components, such as electronic memory and electronic control devices (hereinafter electronic control device(s)), used to control operation of reciprocally movable piston elements 103 (shown in FIG. 2) associated with the fluid injector system 100 described herein. Such piston elements 103 may be reciprocally operable via electro-mechanical drive components such as a ball screw shaft driven by a motor, a voice coil actuator, a rack-and-pinion gear drive, a linear motor, and the like. In some examples, at least some of the mechanical drive components, electrical and power components, and control components may be provided on the base 110.

Figure 1B:
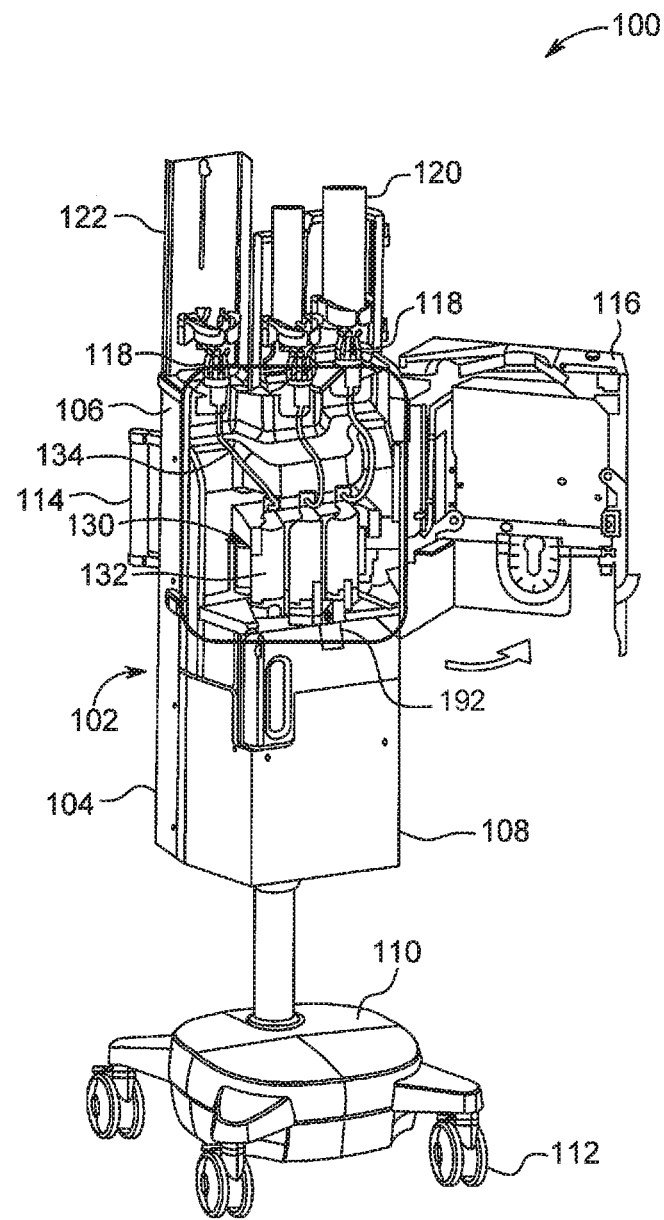
FIG. 1B is a perspective view of the multi-fluid delivery system of FIG. 1A with an access panel in an open position.

With reference to FIG. 1B, and with continued reference to FIG. 1A, the fluid injector system 100 has at least one door 116 that encloses at least some of the mechanical drive components, electrical and power components, and control components. The door 116 is desirably movable between an open position (shown in FIG. 1B) and a closed position (shown in FIG. 1A). In some examples, the door 116 may be lockable.

The fluid injector system 100 further includes at least one bulk fluid connector 118 for connection with at least one bulk fluid source 120. In some examples, a plurality of bulk fluid connectors 118 may be provided. For example, as shown in FIGS. 1A and 1B, three bulk fluid connectors 118 may be provided in a side-by-side or other arrangement. In some examples, the at least one bulk fluid connector 118 may be a spike configured for removably connecting to the at least one bulk fluid source 120, such as a vial, bottle, or a bag. The at least one bulk fluid connector 118 may have a reusable or non-reusable interface with each new bulk fluid source 120. The at least one bulk fluid connector 118 may be formed on the multi-use disposable set, as described herein. The at least one bulk fluid source 120 may be configured for receiving a medical fluid, such as saline, contrast solution, or other medical fluid, for delivery to the fluid injector system 100. The housing 102 may have at least one support member 122 for supporting the at least one bulk fluid source 120 once it is connected to the fluid injector system 100.

With reference to FIG. 1A, the fluid injector system 100 includes one or more user interfaces 124, such as a graphical user interface (GUI) display window. The user interface 124 may display information pertinent to a fluid injection procedure involving the fluid injector system 100, such as flow rate, fluid pressure, and volume remaining in the at least one bulk fluid source 120 connected to the fluid injector system 100. The user interface 124 may be a touch screen GUI that allows an operator to input commands and/or data for operation of the fluid injector system 100. In some examples, the user interface 124 may be a tablet that is detachably connected to the housing 102 and is in wired or wirelessly linked communication with the housing 102. Additionally, the fluid injector system 100 and/or user interface 124 may include at least one control button 126 for tactile operation by an attendant operator of the fluid injector system 100. In certain examples, the at least one control button may be part of a keyboard for inputting commands and/or data by the operator. The at least one control button 126 may be hard-wired to the electronic control device(s) associated with the fluid injector system 100 to provide direct input to the electronic control device(s). The at least one control button 126 may also be graphically part of the user interface 124, such as a touch screen. In either arrangement, the at least one control button 126 desirably provides certain individual control features to the attendant operator of the fluid injector system 100, such as but not limited to: (1) acknowledging that a multi-use disposable set (MUDS) 130 has been loaded or unloaded; (2) locking/unlocking of the MUDS 130; (3) filling/purging of the fluid injector system 100, inputting information and/or data related to the patient and/or injection procedure; and (4) initiating/stopping an injection procedure. The user interface 124 and/or any electronic processing units associated with the fluid injector system 100 may be wired or wirelessly connected to an operation and/or data storage system such as a hospital network system.

With reference to FIG. 1B, the fluid injector system includes the MUDS 130 that is removably connected to the fluid injector system 100 for delivering one or more fluids from the one or more bulk fluid sources 120 to the patient. The fluid injector system 100 includes at least one slot or access port 192 for releasably connecting a SUDS to the MUDS 130, as described herein. The MUDS 130 may include one or more syringes or pumps 132. In some examples, the number of syringes 132 may correspond to the number of bulk fluid sources 120. For example, with reference to FIG. 1B, the MUDS 130 has three syringes 132 in a side-by-side arrangement such that each syringe 132 is fluidly connectable to one of the bulk fluid sources 120. In some examples, one or two bulk fluid sources 120 may be connected to one or more syringes 132 of the MUDS 130. Each syringe 132 may be fluidly connectable to one of the bulk fluid sources 120 by a corresponding bulk fluid connector 118 and an associated MUDS fluid path 134. The MUDS fluid path 134 may have a spike element that connects to the bulk fluid connector 118. In some examples, the bulk fluid connector 118 may be provided directly on the MUDS 130.

Figure 2:
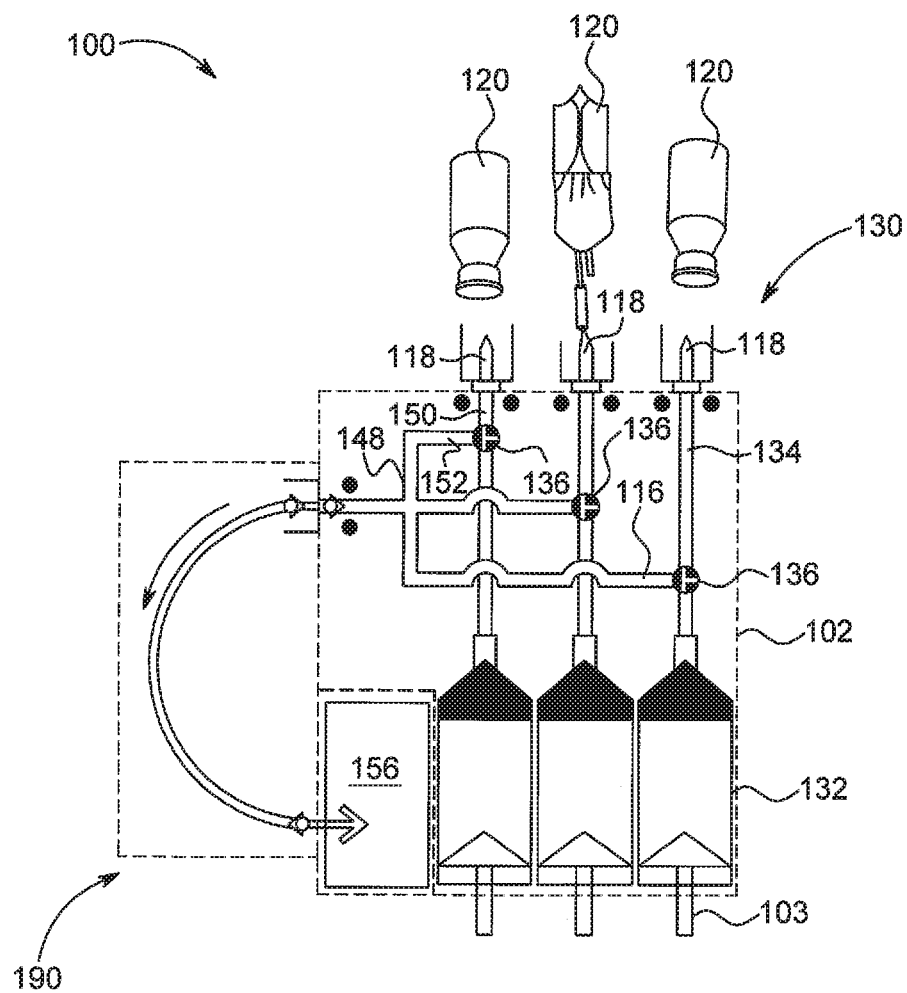
FIG. 2 is a schematic view of various fluid paths within the multi-fluid delivery system of FIG. 1A.
Figure 3A:
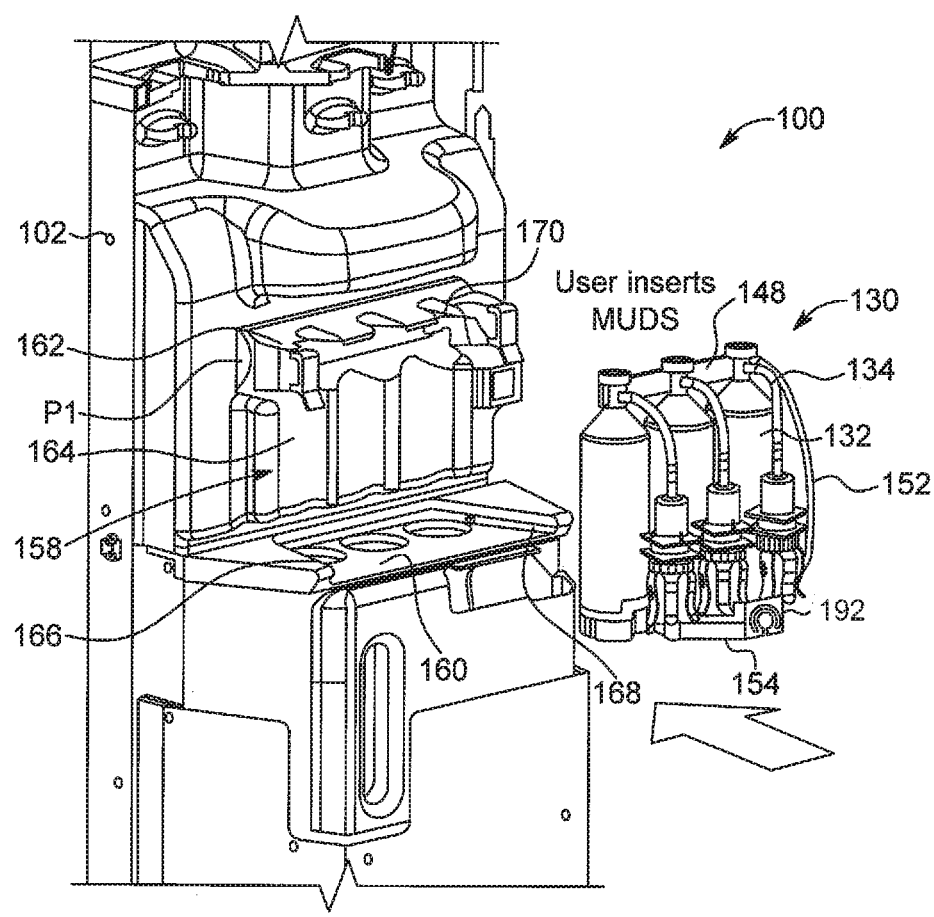
FIG. 3A is a perspective view of a multi-use disposable set (MUDS) during insertion into a receiving slot on a multi-fluid delivery system.
Figure 3B:
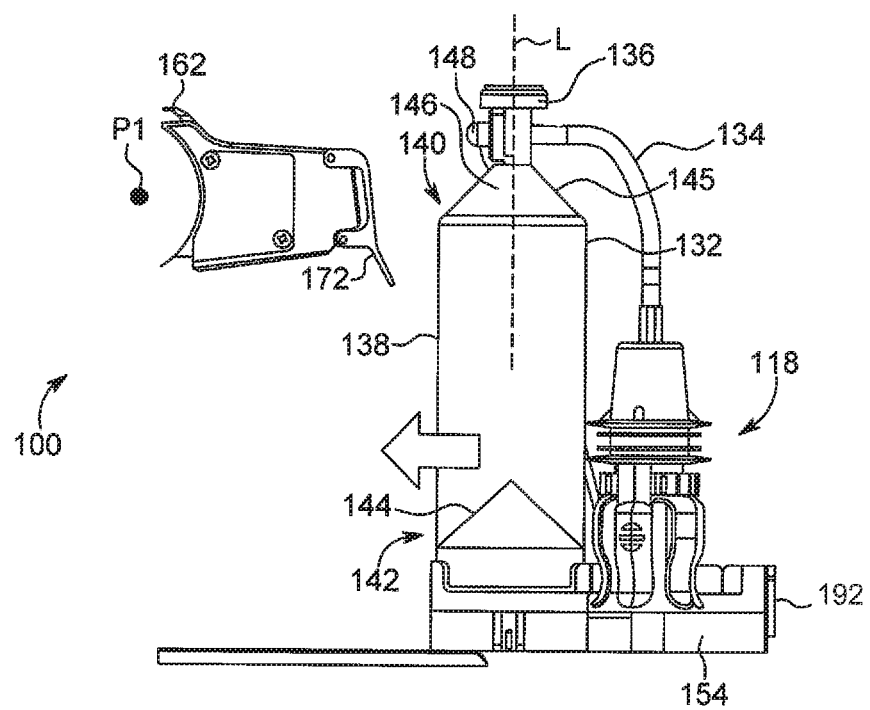
FIG. 3B is a side view of the MUDS of FIG. 3A.

With further reference to FIGS. 2-3A, the MUDS 130 is removably connectable to the housing 102 of the fluid injector system 100. With specific reference to FIG. 3B, the MUDS 130 further includes a frame 154 receiving at least a portion of the proximal end 142 of the at least one syringe 132. In some examples, the frame 154 may be shaped to receive at least a portion of the proximal end 142 of each syringe 132. In some examples, the fluid outlet line 152 may be connected to the frame 154. The frame 154, in some examples, defines at least a portion of the access port 192 for connecting a single-use disposable set to the MUDS 130.

The frame 154 may have a handle for grasping the MUDS 130 during insertion into and removal from the fluid injector system 100. In certain examples, the access port 192 may be formed as part of or adhered/welded to the frame 154 to form a single MUDS 130 unit. The syringes 132 may be removably or non-removably connected to the frame 154. In certain examples, the at least one syringe 132 may be co-molded with the frame 154 or, alternatively, adhered or welded to frame 154.

With further reference to FIG. 3B, each syringe 132 has an elongated, substantially cylindrical syringe body 138 having a front or distal end 140 and a rear or proximal end 142. A syringe plunger 144 is disposed within the syringe body 138 and is reciprocally movable within the syringe body 138 due to movement of a piston element 103 associated with the fluid injector system 100. The distal end 140 of the syringe body 138 is generally conical-shaped and tapers to an apex or cone portion 145 which is adapted to interface with a corresponding apex curve formed in the recess defined in the fluid injector system 100, as described herein. The syringe apex or cone portion 145 is located along a central longitudinal axis L of the syringe body 138. Each syringe 132 has a discharge outlet or conduit 146 at the terminal end of the apex or cone portion 145. The discharge outlet 146 of each syringe 132 is in fluid communication with valve 136 which provides fluid communication with a manifold 148 and the bulk fluid connector 118. The manifold 148 may also provide support for the syringes 132 along with the frame 154 so the syringes 132 can be handled as a single, unitary structure. In some examples, the manifold 148 supports the distal end 140 of each syringe 132 while the frame 154 supports the proximal end 142 of each syringe 132. The syringes 132 may be arranged in a side-by-side orientation, or any other orientation that retains the relative positioning of the syringes 132.

As will be appreciated by one having ordinary skill in the art, it may be desirable to construct at least a portion of the MUDS 130 from a clear medical grade plastic in order to facilitate visual verification that a fluid connection has been established with the fluid injector system 100. Visual verification is also desirable for confirming that no air bubbles are present within various fluid connections. Alternatively, at least a portion of the MUDS 130 and/or door 116 may include windows (not shown) for visualization of the connection between various components. Various optical sensors (not shown) may also be provided to detect and verify the connections. Additionally, various lighting elements (not shown), such as light emitting diodes (LEDs) may be provided to actuate one or more optical sensors and indicate that a suitable connection has been established between the various components.

With specific reference to FIG. 2, a schematic view of various fluid paths of the fluid injector system 100 is provided. The MUDS 130 may include one or more valves 136, such as stopcock valves, for controlling which medical fluid or combinations of medical fluids are withdrawn from the multi-dose bulk fluid source 120 and/or are delivered to a patient through each syringe 132. In some examples, the one or more valves 136 may be provided on the distal end 140 of the plurality of syringes 132 or on the manifold 148. The manifold 148 may be in fluid communication via valves 136 and/or syringes 132 with a first end of the MUDS fluid path 134 that connects each syringe 132 to the corresponding bulk fluid source 120. The opposing second end of the MUDS fluid path 134 may be connected to the respective bulk fluid connector 118 that is configured for fluidly connecting with the bulk fluid source 120. Depending on the position of the one or more valves 136, fluid may be drawn into the one or more syringes 132, or it may be delivered from the one or more syringes 132. In a first position, such as during the filling of the syringes 132, the one or more valves 136 are oriented such that fluid flows from the bulk fluid source 120 into the desired syringe 132 through a fluid inlet line 150, such as a MUDS fluid path. During the filling procedure, the one or more valves 136 are positioned such that fluid flow through one or more fluid outlet lines 152 or manifold 148 is blocked. In a second position, such as during a fluid delivery procedure, fluid from one or more syringes 132 is delivered to the manifold 148 through the one or more fluid outlet lines 152 or syringe valve outlet ports. During the delivery procedure, the one or more valves 136 are positioned such that fluid flow through one or more fluid inlet lines 150 is blocked. The one or more valves 136, fluid inlet lines 150, and/or fluid outlet lines 152 may be integrated into the manifold 148. The one or more valves 136 may be selectively positioned to the first or second position by manual or automatic handling. For example, the operator may position the one or more valves 136 into the desired position for filling or fluid delivery. In other examples, at least a portion of the fluid injector system 100 is operable for automatically positioning the one or more valves 136 into a desired position for filling or fluid delivery based on input by the operator.

Referring again to FIG. 2, in some examples, the fluid outlet line 152 may also be connected to a waste reservoir 156 on the fluid injector system 100. The waste reservoir 156 is desirably separate from the syringes 132 to prevent contamination. In some examples, the waste reservoir 156 is configured to receive waste fluid expelled from the syringes 132 during, for example, a priming operation. The waste reservoir 156 may be removable from the housing 102 in order to dispose of the contents of the waste reservoir 156. In other examples, the waste reservoir 156 may have a draining port (not shown) for emptying the contents of the waste reservoir 156 without removing the waste reservoir 156 from the housing 102. In some examples, the waste reservoir 156 is provided as a separate component from the MUDS 130.

With the foregoing description of the fluid injector system 100 and the MUDS 130 in mind, exemplary loading of the MUDS 130 into a receiving space 158 (shown in FIG. 3A) on the housing 102 will now be described with reference to FIGS. 3A-4C. In the following discussion, it is assumed that the MUDS 130 may be connected to the fluid injector system 100 for use with a single patient or multiple patients. Referring initially to FIG. 3A, the receiving space 158 has a bottom plate 160 separated from a top plate 162 by a rear sidewall 164. The bottom plate 160 has a plurality of openings 166 through which the piston elements 103 (shown in FIG. 2) of the fluid injector system 100 extend to engage the respective plungers 144 of the MUDS 130. At least one bottom guide 168 is formed on the bottom plate 160 for guiding the frame 154 of the MUDS 130 as the MUDS 130 is loaded into the fluid injector system 100. In some examples, the bottom guide 168 may be configured as a pair of walls raised relative to the bottom plate 160 and narrowing in an insertion direction toward the rear sidewall 164. During insertion, the bottom guide 168 defines a guiding surface that locates the frame 154 of the MUDS 130 and guides the frame 154 toward the rear sidewall 164 of the receiving space 158. In this manner, the MUDS 130 can be aligned into the receiving space 158 even when MUDS 130 is initially misaligned with receiving space 158.

With reference to FIG. 3B, and with continued reference to FIG. 3A, the top plate 162 is configured to receive the distal end 140 of the at least one syringe 132. The top plate 162 has one or more syringe slots 170 (shown in FIG. 3A) that are shaped to receive at least a portion of the distal end 140 of the syringes 132. In some examples, when the MUDS 130 is inserted into the receiving space 158, the syringe slots 170 of the top plate 162 may be disposed between the distal end 140 of the at least one syringe 132 and the manifold 148. The top plate 162 may be rotatable about a pivot point P1 (shown in FIG. 3B) or it may be movable in a vertical direction relative to the MUDS 130. In a first position, such as during loading of the MUDS 130 into the receiving space 158, the top plate 162 may be raised such that the apex or cone portion 145 of the at least one syringe 132 clears a lower surface of the top plate 162. In some examples, the top plate 162 can default to the first position each time the MUDS 130 is removed from the receiving space 158, such as by a biasing mechanism. In other examples, the top plate 162 can be urged to the first position as the apex or cone portion 145 of the at least one syringe 132 engages the at least one syringe slot 170.

Figure 4A:
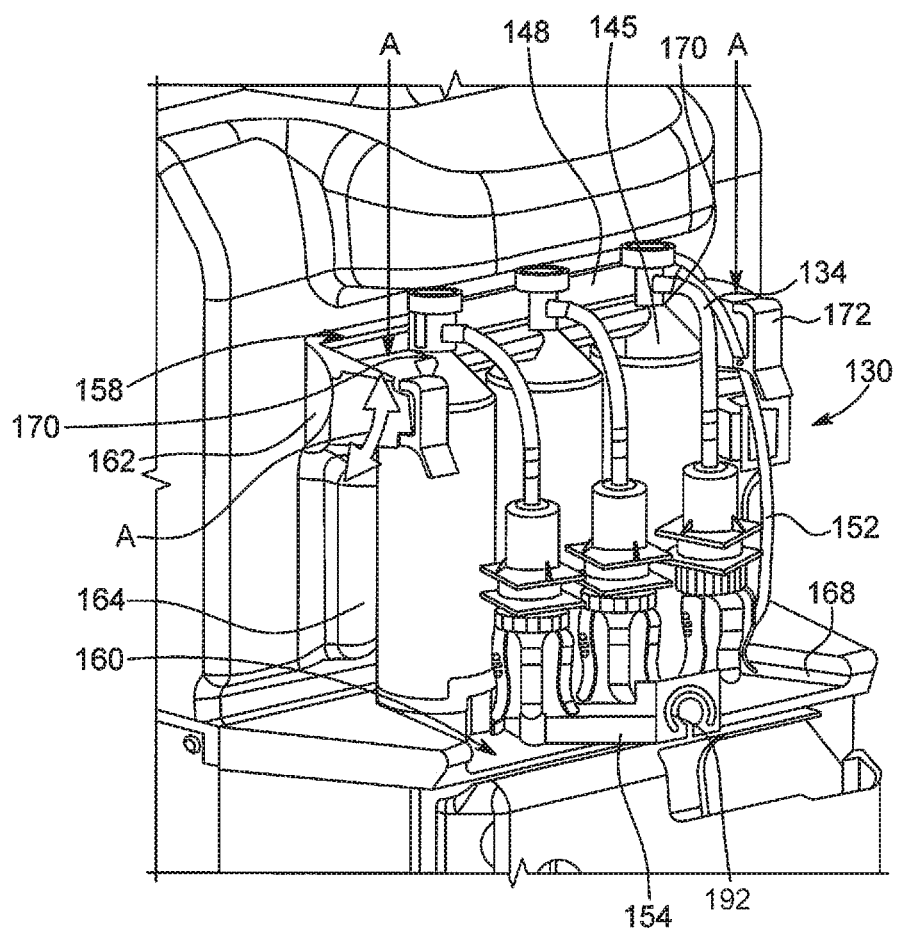
FIG. 4A is a perspective view of the MUDS installed into the receiving slot on the multi-fluid delivery system of FIG. 3A.
Figure 4B:
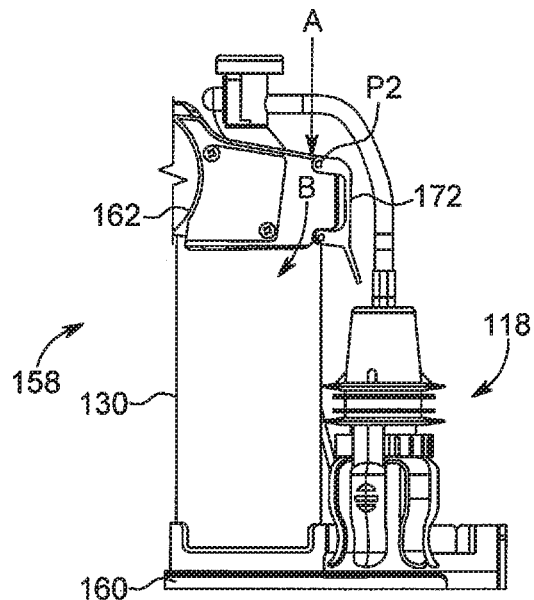
FIG. 4B is a side view of the MUDS of FIG. 4A.
Figure 4C:
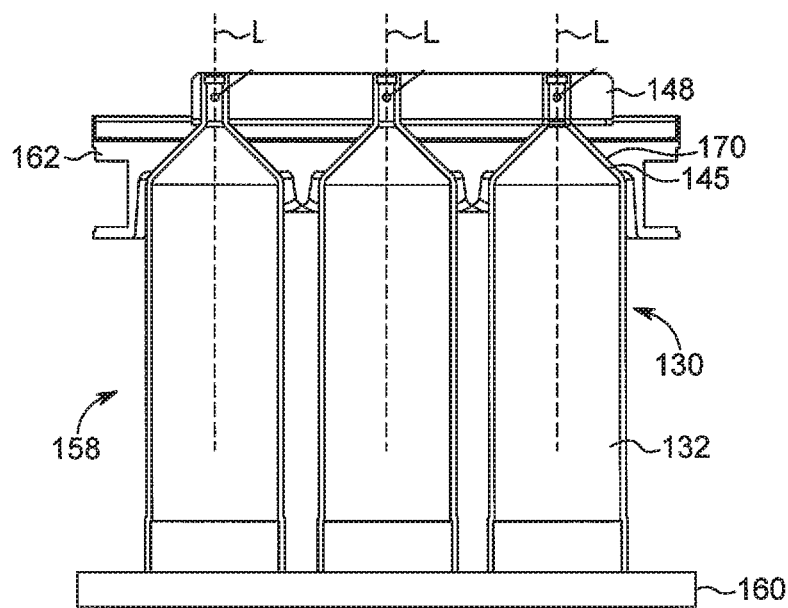
FIG. 4C is a cross-sectional view of the MUDS of FIG. 4A.

As the MUDS 130 engages the rear sidewall 164, such as shown in FIG. 4A, the MUDS 130 can be locked in the receiving space 158 by moving the top plate 162 to a second position. In the second position, the top plate 162 is lowered such that the apex or cone portion 145 of the at least one syringe 132 engages the lower surface of the top plate 162. In some examples, the top plate 162 can be urged to the second position by a biasing mechanism (not shown). In other examples, the top plate 162 can be manually moved to the second position by pivoting the top plate 162 in a direction of arrow A shown in FIGS. 4A-4B. The top plate 162 can be locked relative to the MUDS 130 to prevent removal of the MUDS 130 from the receiving space 158 by a latch 172. The latch 172 may be operable to prevent the top plate 162 from rotating about the pivot point P1. The latch 172 may be a spring-loaded latch that is pivotable about a pivot point P2 in a direction of arrow B shown in FIG. 4B. In some examples, the latch 172 may be an over-center, spring-loaded latch that is pivotable about a pivot point P2. With reference to FIG. 4C, when the MUDS 130 is locked within the receiving space 158, the lower surface of the top plate 162 engages the apex or cone portion 145 of the at least one syringe 132. In the locked position, the longitudinal axis L of each syringe 132 is aligned with a center of each syringe slot 170. Removal of the MUDS 130 from the receiving space 158 when the top plate 162 is in the locked position is prevented by the engagement of the lower surface of the top plate 162 with the apex or cone portion 145 of the at least one syringe 132. Once locked, the top plate 162 substantially retains the syringes 132 from moving axially during an injection procedure.

Figure 5:
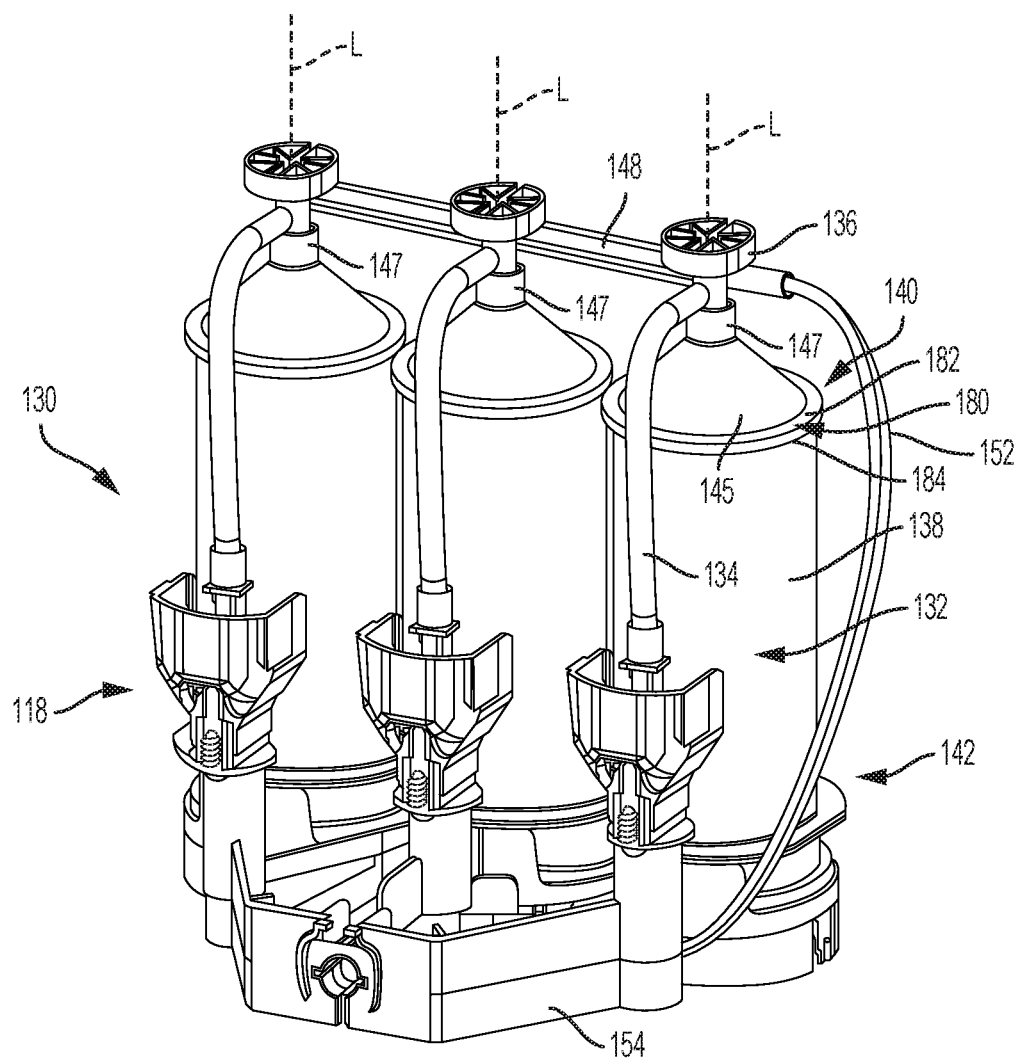
FIG. 5 is a perspective view of a MUDS having a plurality of syringes according to one example of the present disclosure.
Figure 6A:
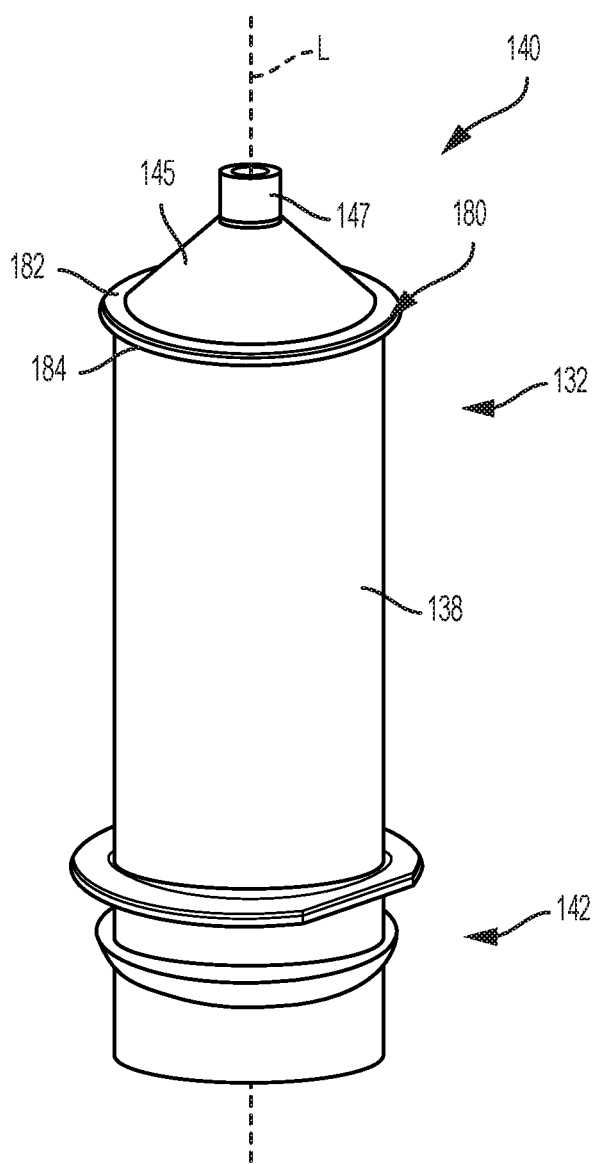
FIG. 6A is a perspective view of a single syringe configured for use with the MUDS according to a one example of the present disclosure.

With reference to FIGS. 5 and 6A, according to one example of the disclosure, the syringes 132 used in the MUDS 130 may include a stabilizing element 180 provided on the distal end 140 of each syringe 132. In this example shown in FIG. 5, another configuration of the MUDS 130 includes a plurality of bulk fluid connectors 118, a frame 154, a plurality of valves 136 provided on a manifold 148, a fluid path 134 between each valve 136 and the bulk fluid connectors 118, and a fluid outlet line 152. The stabilizing element 180 may extend around at least a portion of the distal end 140 of each syringe 132. In another example, the stabilizing element 180 may extend around at least a portion of the distal end 140 of the syringe 132 around the longitudinal axis L. It is contemplated that the stabilizing element 180 may be continuous around the entire circumference or may include a plurality of separate sections isolated by spaces that are defined between each section. The stabilizing element 180 may be positioned at a proximal end of the cone portion 145 of the syringe 132 or any part of the cone portion 145 up to the nozzle 147. In this example, the stabilizing element 180 may have an inner diameter that substantially corresponds to the outer diameter of the syringe body 138. The stabilizing element 180 may be a ring that is formed integrally with the syringe body 138 or may be removably or non-removably attached to the syringe body 138, such as by adhesive, interference fit, welding, or other mechanical connections. The stabilizing element 180 may have a substantially planar upper surface 182 and a substantially planar bottom surface 184. In one example, the upper surface 182 may extend substantially perpendicular to the longitudinal axis L of the syringe 132. The planar upper surface 182 is provided to stabilize the syringe 132 when the top plate 162 of the fluid injector system 100 is closed on the distal end 140 of the syringe 132 to lock the MUDS 130 within the fluid injector system 100. In this manner, the upper surface 180 is oriented substantially perpendicular to the longitudinal axis of the movable piston element 103 such that the movable piston element 103 does not impart a radially oriented force on the syringe 132. The stabilizing element 180 may be made of the same material as the syringe 132. In one example, stabilizing element 180 may be made of a transparent, medical-grade plastic.

During insertion of the MUDS 130 into the fluid injector system 100, the top plate 162 is rotated downwards to bring the syringe slots 170 into engagement with the syringes 132 in the MUDS 130. As can often occur during the insertion procedure, the top plate 162 may contact the distal ends 140 of the syringes 132 and position the syringes 132 such that the longitudinal axis L of the syringe 132 is out of alignment with the longitudinal axis of the movable piston elements 103. The top plate 162 may contact the cone portion 145 of the syringes 132 and push the syringes 132 into an off-center position such that the syringes 132 are angled relative to the longitudinal axis of the movable piston elements 103. Due to the angled surface of the cone portion 145 of the syringes 132, syringe slots 170, and resulting forces from fluid delivery (fluid pressure), the top plate 162 may move the syringes 132 away from a desired operating position. For example, when the piston plunger assembly of one or more of the syringes is 132 is moved in a distal direction, such as during a fluid delivery process, the pressure one the fluid and syringes may shift the MUDS to an off-center or tilted position resulting in potential fluid leakage or "blow by" between the circumferential rim of the plunger and the inner syringe wall. To avoid or correct the potential tendency for the MUDS unit to be forced out of alignment with the longitudinal axis, the stabilizing element 180 of the distal end 140 of each syringe 132 ensures that the top plate 132 rests on a planar or flat surface to assure alignment of the longitudinal axis L of the syringe 132 with the longitudinal axis of the movable piston elements 103. As the top plate 162 is rotated downwards towards the syringes 132, the top plate 162 may contact the stabilizing element 180, which provides a flat, planar surface that provides an increased surface area for the top plate 162 to contact.

Figure 6B:
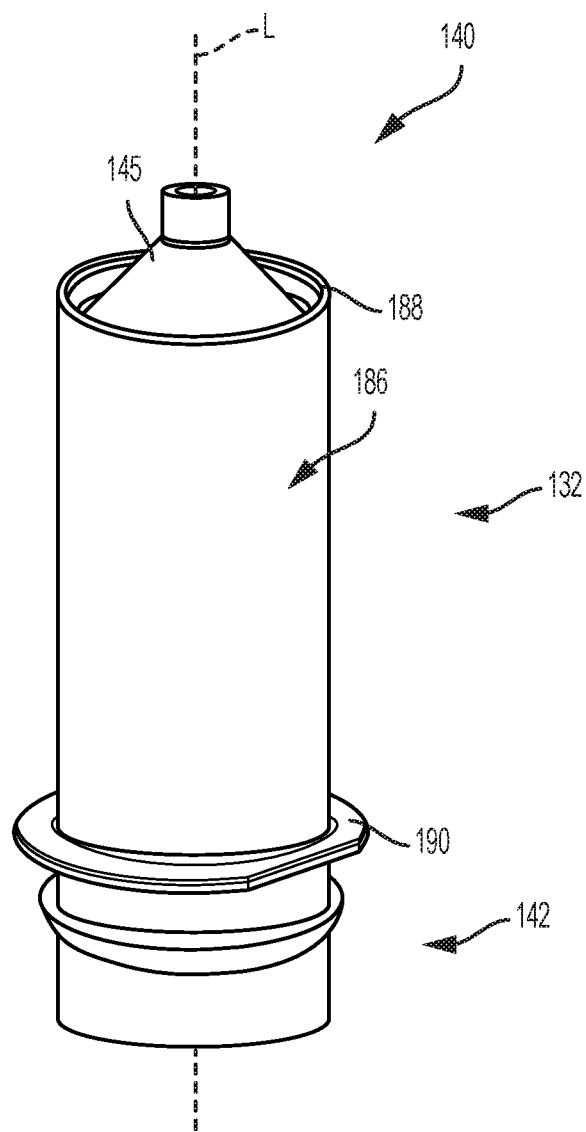
FIG. 6B is a perspective view of a single syringe configured for use with the MUDS according to a another example of the present disclosure.

With reference to FIG. 6B, another example of the stabilizing element 186 is shown on a syringe 132. In this example, the stabilizing element 186 may be a sleeve that is formed or provided around the body 138 (covered in FIG. 6B by the stabilizing element 186) of the syringe 132. The stabilizing element 186 may be formed integrally with the body 138, may be removably or non-removably attached to the body 138, such as by adhesion, welding, or friction fit with the body 138. The stabilizing element 186 may include a planar upper surface 188 upon which the top plate 162 of the fluid injector system 100 may contact when the MUDS 130 has been inserted into the fluid injector system 100. In one example, the upper surface 188 may extend substantially perpendicular to the longitudinal axis L of the syringe 132. The stabilizing element 186 may be substantially cylindrical with an inner diameter that is slightly greater than the outer diameter of the body 138. In another example, the inner diameter of the stabilizing element 186 may be slightly smaller than the outer diameter of the body 138, but may be resilient to form a friction fit with the body 138. A distal end of the stabilizing element 186 may be positioned adjacent to the cone portion 145 of the syringe 132. A proximal end of the stabilizing element 186 may contact a flange 190 provided on the proximal end 142 of the syringe 132. The stabilizing element 186 may be made of the same material as the syringe 132. In one example, the stabilizing element 186 may be made of a transparent, medical-grade plastic. Similar to the stabilizing element 180 shown in FIG. 6A, the stabilizing element 186 may be provided on the syringe 132 to stabilize the syringe 132 upon insertion of the MUDS 130 into the fluid injector system 100. The top plate 162 of the fluid injector system 100 may contact the planar upper surface 188 of the stabilizing element 186 to hold the syringe 132 in an upright, centered position relative to the fluid injector system 100. In another example, the stabilizing element 186 may be a part of the syringe body 138 of the syringe 132, extending axially along the longitudinal axis L, protruding from the cone portion 145 of the syringe 132.

Figure 6C:
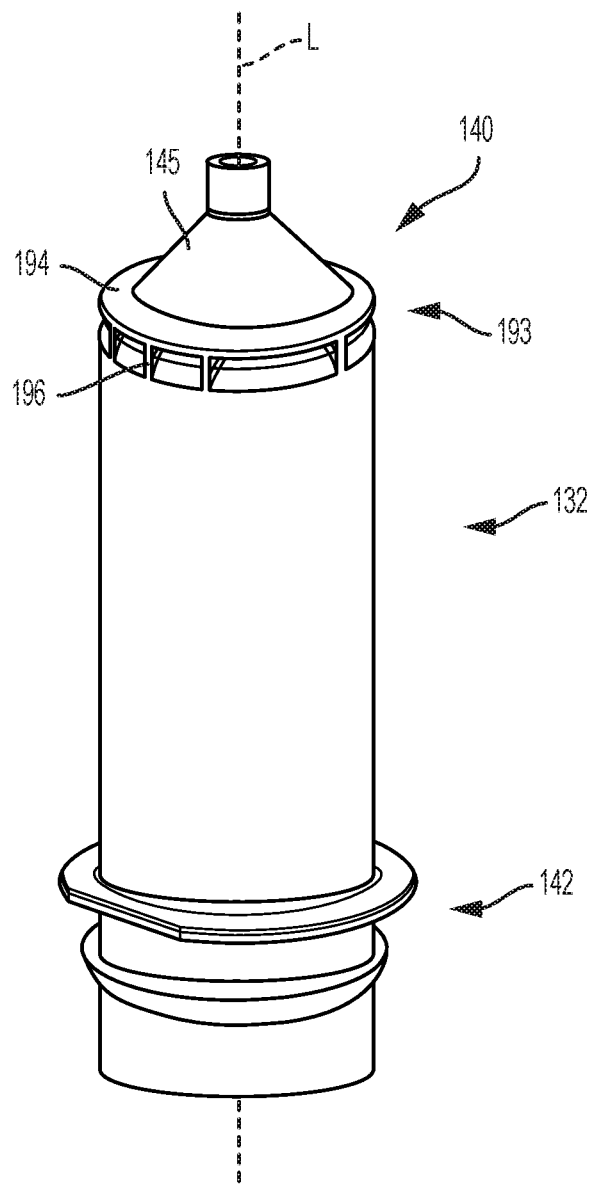
FIG. 6C is a perspective view of a single syringe configured for use with the MUDS according to a another example of the present disclosure.

With reference to FIG. 6C, another example of the stabilizing element 193 is shown on a syringe 132. The stabilizing element 193 may include a substantially planar member 194 and a plurality of webs 196 that connect the stabilizing element 193 to the syringe 132. The planar member 194 may include an upper surface that extends substantially perpendicular to the longitudinal axis L of the syringe 132. An inner circumferential surface of the planar member 194 may be integrally (i.e., monolithically) formed on or removably or non-removably attached to the cone portion 145 of the syringe 132. It is also contemplated that the inner circumferential surface of the planar member 194 may not be connected to the syringe 132, but may contact the cone portion 145 of the syringe 132. A bottom surface of each web 196 may be integrally formed on the syringe 132 or may be removably or non-removably attached to the syringe 132. An upper surface of each web 196 may be integrally formed on or remoavbly or non-removably connected to a bottom surface of the planar member 194. In one example, the webs 196 may be triangular in shape. The stabilizing element 193 may be made of the same material as the syringe 132. In one example, the stabilizing element 193 may be made of a transparent, medical-grade plastic. Similar to the stabilizing element 180 shown in FIG. 6A, the stabilizing element 193 may be provided on the syringe 132 to stabilize the syringe 132 within the MUDS 130 upon insertion of the MUDS 130 into the fluid injector system 100. The top plate 162 of the fluid injector system 100 may contact the planar member 194 of the stabilizing element 193 to hold the syringe 132 in an upright, centered position relative to the fluid injector system 100.

Figure 6D:
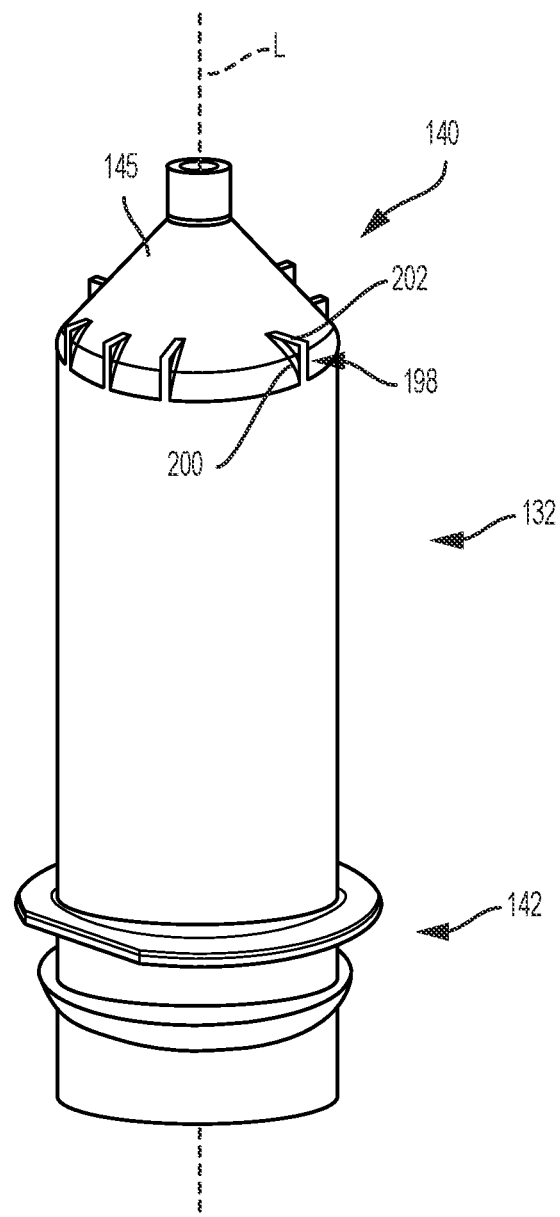
FIG. 6D is a perspective view of a single syringe configured for use with the MUDS according to a another example of the present disclosure.

With reference to FIG. 6D, another example of a stabilizing element 198 is shown on a syringe 132. The stabilizing element 198 is similar to the webs 196 depicted in FIG. 6C. In one example, at least two stabilizing elements 198 may be provided on the syringe 132. It is also contemplated that a plurality of stabilizing elements 198 may be provided around the outer circumferential surface of the syringe 132. The stabilizing element 198 is substantially triangular and includes a bottom surface 200 that is formed integrally with or adhesively attached to the cone portion 145 of the syringe 132. The stabilizing element 198 may have a planar upper surface 202 that extends outwardly from the cone portion 145. The upper surface 202 may extend perpendicular to the longitudinal axis L of the syringe 132. The stabilizing element 198 may be made of the same material as the syringe 132. In one example, the stabilizing element 198 may be made of a transparent, medical-grade plastic. Similar to the stabilizing element 180 shown in FIG. 6A, the stabilizing element 198 may be provided on the syringe 132 to stabilize the syringe 132 upon insertion of the MUDS 130 into the fluid injector system 100. The top plate 162 of the fluid injector system 100 may contact the upper surface 202 of the stabilizing element 198 to hold the syringe 132 in an upright, centered position relative to the fluid injector system 100.

Figure 6E:
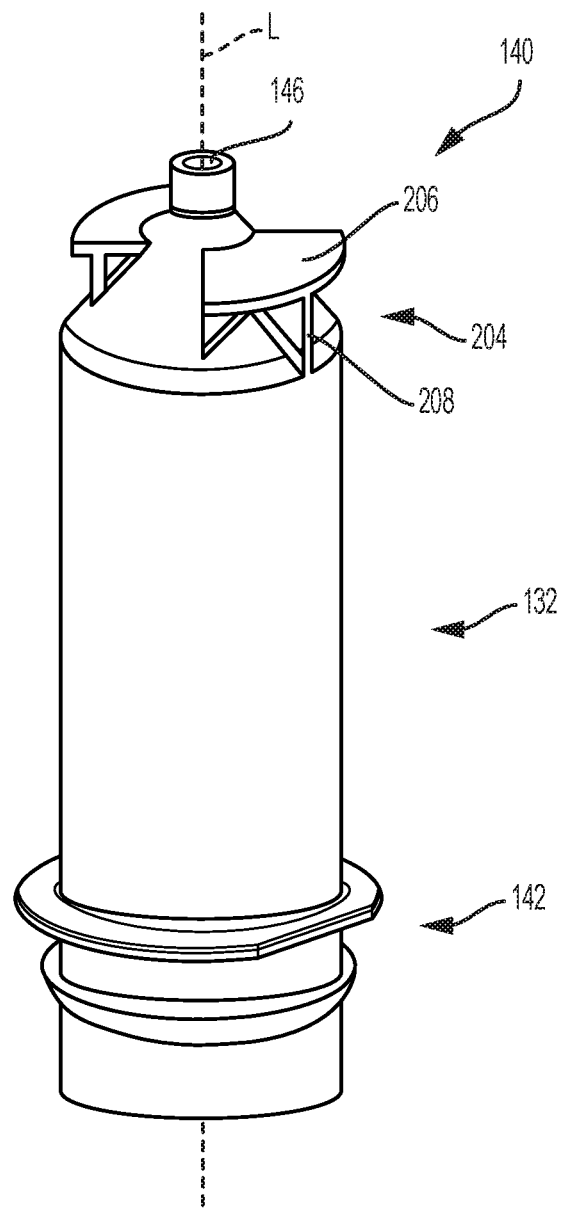
FIG. 6E is a perspective view of a single syringe configured for use with the MUDS according to another example of the present disclosure.

With reference to FIG. 6E, another example of a stabilizing element 204 is shown on a syringe 132. In one example, at least two stabilizing elements 204 may be provided on the syringe 132. In another example, more than two stabilizing elements 204 may be provided on the syringe 132. It is also contemplated that the stabilizing element 204 may extend around the entire outer circumferential surface of the cone portion 145 of the syringe 132. The stabilizing element 204 may include a planar member 206 and a plurality of webs 208 provided to connect the planar member 206 to the syringe 132. The stabilizing element 204 may be integrally formed on or removably or non-removably attached to the syringe 132. The stabilizing element 204 may be provided entirely on the cone portion 145 of the syringe 132. The planar member 206 may include an upper surface that extends substantially perpendicular to the longitudinal axis L of the syringe 132. The planar member 206 may be positioned adjacent the discharge conduit 146 of the syringe 132. An inner circumferential surface of the planar member 206 may be integrally formed on or removably or non-removably attached to the cone portion 145 of the syringe 132. It is also contemplated that the inner circumferential surface of the planar member 206 may not be connected to the syringe 132, but may contact the cone portion 145 of the syringe 132. A bottom surface of each web 208 may be integrally formed on the syringe 132 or may be removably or non-removably attached to the syringe 132. An upper surface of each web 208 may be integrally formed on or removably or non-removably connected to a bottom surface of the planar member 206. In one example, the webs 208 may be triangular in shape. The stabilizing element 204 may be made of the same material as the syringe 132. In one example, the stabilizing element 204 may be made of a transparent, medical-grade plastic. Similar to the stabilizing element 180 shown in FIG. 6A, the stabilizing element 204 may be provided on the syringe 132 to stabilize the syringe 132 within the MUDS 130 upon insertion of the MUDS 130 into the fluid injector system 100. The top plate 162 of the fluid injector system 100 may contact the planar member 206 of the stabilizing element 204 to hold the syringe 132 in an upright, centered position relative to the fluid injector system 100.

Figure 7A:
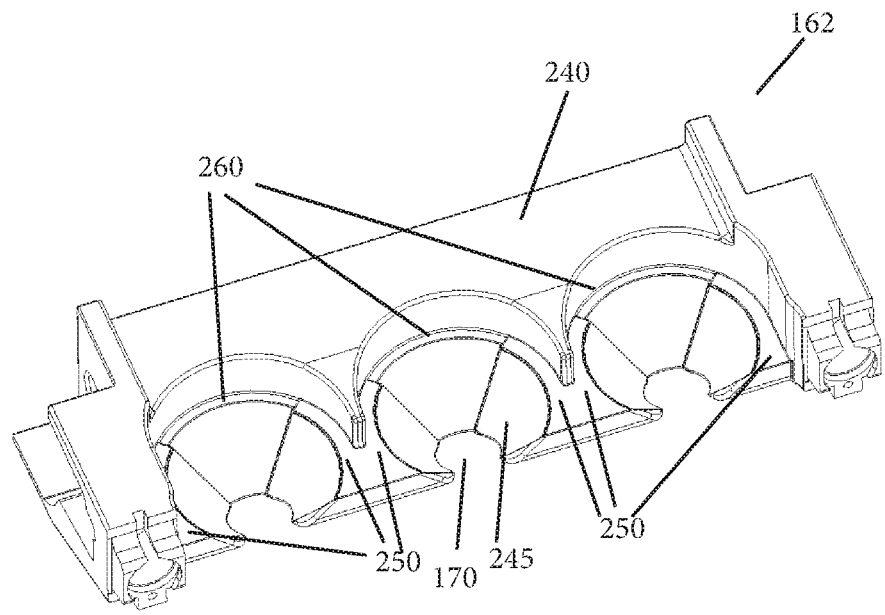
FIG. 7A is a bottom view of the top plate associated with the injector for restraining the MUDS according to one example of the present disclosure.
Figure 7B:
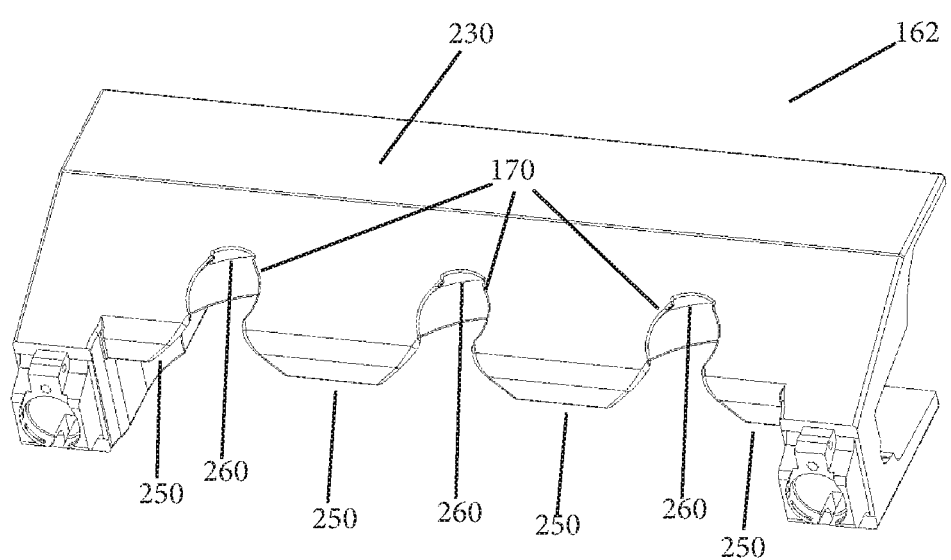
FIG. 7B is a top view of the top plate associated with the injector for restraining the MUDS according to one example of the present disclosure.

FIGS. 7A, 7B illustrate an embodiment of the top side and the bottom side of the top plate 162. Referring first to FIG. 7A, top plate 162 has a bottom surface 240 and three syringe slots 170 for receiving the distal ends of syringes 132. Each syringe slot 170 has an interior conical portion 245 and stabilizing element contact surface 250 and an optional recessed surface 260. The stabilizing element contact surface 250 has a surface perpendicular to the longitudinal axis L of the MUDS when the top plate 162 is in the inserted and locked position, such that the stabilizing element contact surface 250 is in flush surface-to-surface contact with the planar upper surface (182, 188, 194, 202, or 206) of the stabilizing element 180, 193, 186, 198, or 204, respectively). The flush surface-to-surface contact between the stabilizing element contact surface 250 and the planar upper surface prevents tilting or off-center alignment of the MUDS relative the longitudinal axis of the piston path. Optional recessed surface 260 comprises a recessed area relative to the stabilizing element contact surface 250 near the back side of top plate 162 and prevents contact with the syringe stabilizing element during the loading process as the top plate 162 is lowered to engage the MUDS. This may allow for balanced loading of the syringe stabilizing element without displacing or miss-aligning the MUDS as the top plate 162 is lowered due to contact between the stabilizing element upper surface and the rear portion of syringe slot 170. Referring to FIG. 7B, a top surface 230 of top plate 162 is illustrated. Syringe slots 170 can be seen along with recessed surfaces 260 at the rear portion of syringe slots 170. The edge of the stabilizing element contact surface 250 may be seen near the front of syringe slots 170.

While several examples of multi-use disposable sets and syringes therefor are shown in the accompanying figures and described hereinabove in detail, other examples will be apparent to, and readily made by, those skilled in the art without departing from the scope and spirit of the disclosure. For example, it is to be understood that this disclosure contemplates that, to the extent possible, one or more features of any example can be combined with one or more features of any other example. Accordingly, the foregoing description is intended to be illustrative rather than restrictive.

The invention claimed is:

1. A multi-use disposable set (MUDS) comprising:
a plurality of syringes, each syringe having a syringe body, a proximal end, a distal end spaced apart from the proximal end along a longitudinal axis of the syringe body, a cone portion and a nozzle extending distally from the distal end of the syringe body, and a stabilizing element provided on the distal end, the cone portion being monolithically formed with the syringe body, the stabilizing element comprising a continuous ring that extends around an entire outer circumferential surface of a proximal end of the cone portion on the distal end, the stabilizing element having an engagement surface extending substantially perpendicular to the longitudinal axis of the syringe body, wherein the engagement surface is configured to stabilize a vertical alignment of each syringe of the plurality of syringes when a planar surface of a top plate of a fluid injector system defining at least one syringe slot is moved into a closed position to contact the engagement surface of each of the syringes, wherein an outer diameter of the stabilizing element is greater than an outer diameter of the syringe body, and wherein the stabilizing element is integrally formed on the syringe body;
a frame for receiving at least a portion of the proximal end of each syringe of the plurality of syringes prior to the top plate of the fluid injector system being moved into engagement with the engagement surface of each syringe, and for loading into a bottom guide of the fluid injector to align the MUDS in a receiving space of the fluid injector; and a manifold in fluid communication with the distal end of each syringe of the plurality of syringes.

2. The MUDS of claim 1, wherein each engagement surface is configured to provide a stable verticle alignment of the respective syringe with a corresponding movable piston element of the fluid injector system as a planar surface on the top plate of the fluid injector system contacts the stabalizing element.

* * * * *

UNITED STATES PATENT AND TRADEMARK OFFICE
CERTIFICATE OF CORRECTION

| | |
|---|---|
| PATENT NO. | : 11,738,152 B2 |
| APPLICATION NO. | : 16/304850 |
| DATED | : August 29, 2023 |
| INVENTOR(S) | : Haury et al. |

It is certified that error appears in the above-identified patent and that said Letters Patent is hereby corrected as shown below:

In the Specification

In Column 2, Line 4, delete "deliver" and insert -- delivery --, therefor.

In Column 11, Line 47, delete "one" and insert -- on --, therefor.

In Column 14, Line 13, delete "the" and insert -- to the --, therefor.

In the Claims

In Column 15, Line 7, in Claim 2, delete "verticle" and insert -- vertical --, therefor.

In Column 15, Line 11, in Claim 2, delete "stabalizing" and insert -- stabilizing --, therefor.

Signed and Sealed this
Fourteenth Day of November, 2023

Katherine Kelly Vidal
*Director of the United States Patent and Trademark Office*